United States Patent [19]

Chiang et al.

[11] Patent Number: 4,689,296
[45] Date of Patent: Aug. 25, 1987

[54] METHOD OF PREPARING NOVEL THERMOSTABLE TRANSGLUCOSIDASE

[75] Inventors: John P. Chiang, Elkhart; Oreste J. Lantero, Jr., Goshen, both of Ind.

[73] Assignee: Miles Laboratories, Inc., Elkhart, Ind.

[21] Appl. No.: 779,051

[22] Filed: Sep. 23, 1985

[51] Int. Cl.[4] .................. C12P 19/18; C12N 9/10; C12N 9/34; C12R 1/645
[52] U.S. Cl. .................................. 435/97; 435/193; 435/205; 435/911
[58] Field of Search .................. 435/97, 193, 205

[56] References Cited

U.S. PATENT DOCUMENTS

| | | | |
|---|---|---|---|
| 3,042,584 | 7/1962 | Kooi et al. | 435/193 X |
| 3,301,768 | 1/1967 | Smiley | 435/205 |
| 3,318,782 | 5/1967 | Garbutt | 435/205 |
| 3,483,084 | 12/1969 | Sternberg | 435/205 |
| 4,247,637 | 1/1981 | Tamura et al. | 435/96 |
| 4,587,215 | 5/1986 | Hirsh | 435/96 |

*Primary Examiner*—Lionel M. Shapiro
*Attorney, Agent, or Firm*—Jerome L. Jeffers

[57] ABSTRACT

Disclosed is a method for preparing transglucosidase comprising culturing a strain of *Talaromyces duponti* in a suitable nutrient growth medium and isolating the transglucosidase therefrom. Also disclosed is the transglucosidase produced by *T. duponti*.

9 Claims, No Drawings

METHOD OF PREPARING NOVEL THERMOSTABLE TRANSGLUCOSIDASE

This invention relates to a novel method of preparing transglucosidase from *Talaromyces duponti*. The transglucosidase, which is very thermostable, is useful in the conversion of maltose to panose and iomaltose.

BACKGROUND OF THE INVENTION

Transglucosidase (also known as 1,4-alpha-D-glucan-6-alpha-D-glucosyltranferase and as transglucosylase) has been obtained from various microorganisms. It is an enzyme which causes the formation of the trisaccharide panose and the disaccharide isomaltose from maltose by bond cleavage and bond formation. These oligosaccharides are non-fermentable and thus find application in the food, soft drink and sake industries, as well as in the formulation of new foods. See, for instance, Nunokawa et al, Japanese Pat. No. Sho 56(1981)-27236. They describe a method for producing transglucosidase and glucoamylase by culturing a strain of *Aspergillus saitoi* or *A. usami*. The culture filtrate is passed through a resin-containing column which retains the transglucosidase while the glucoamylase passes in the effluent. The transglucoside is removed from the resin with an acetate buffer solution at pH 5.5. Also, Pazur et al in "The Isolation and the Mode of Action of a Fungal Transglucosylase", from the Department of Biochemistry and Nutrition, University of Nebraska, Lincoln, Neb., Archives of Biochemistry and Biophysics, Volume 93, pages 43–49 (1961) describe a method for obtaining the transglucosylase of *Aspergillus niger* that involves separating this enzyme from the other co-produced carbohydrases by chromotography and adsorption on DEAE-cellulose (diethylaminoethyl-cellulose), starch, and carboxymethylcellulose.

On the other hand, Tamura et al in U.S. Pat. No. 4,247,637 describe a process for the production of thermostable glucoamylase from a strain of *Talaromyces duponti*, which involves culturing the strain in a nutrient medium and isolating the enzyme. After they culture the strain and remove the mycelia by filtration, they pass the filtrate through active clay and find the glucoamylase in the effluent. There is no recognition whatsoever by Tamura et al that *Talaromyces duponti* will also secrete transglucosidase, let alone a very thermostable transglucosidase.

Accordingly, it has been discovered by the present inventors that thermostable transglucosidase can be prepared by culturing cells of *Talaromyces duponti* in a suitable nutrient medium.

SUMMARY OF THE INVENTION

The present invention provides a method for preparing transglucosidase comprising culturing a strain of *Talaromyces duponti* in a suitable nutrient growth medium and isolating the transglucosidase therefrom. The invention also provides transglucosidase produced by a fungus of the species *T. duponti*.

DETAILED DESCRIPTION OF THE INVENTION

The present invention specifically relates to the enzyme transglucosidase from the fungal species *T. duponti*. The enzyme is provided by the fermentation in a nutrient growth medium of this microorganism. After fermentation during which the enzyme is secreted, the biomass may be removed from the fermentation broth by any liquid solid separatory technique, such as by filtration or by centrifugation with decantation, to provide an enzyme-containing solution.

Typically, the media that are employed for culturing ordinary molds are used as the nutritional source for the fermentation of *T. duponti*. Various carbon sources are well known and may be selected from starches, molasses, cornmeal, and the like. The nitrogen sources are also commonly known and typical examples are soy, cottonseed, peptone, corn steep liquor, yeast extract, and the like. Sulfate and/or chloride salts are also used in the fermentation media, such as magnesium sulfate, calcium chloride, sodium chloride and potassium chloride. Often, phosphate salts are also employed since they function as buffering agents as well. Additionally, the pH of the fermentation media may be adjusted, preferably within a range close to neutral, with bases such as sodium hydroxide or potassium hydroxide and/or with acids such as hydrochloric acid or acetic acid.

The conditions of pH, time and temperature are well known in the art for culturing molds. The pH must be within a range from approximately 3 to approximately 9, and more preferably between approximately 5 and approximately 8. A very advantageous pH for the culture media is close to neutrality. The fermentation is conducted for anywhere from approximately 2 to 10 days, more preferably approximately 4 to 8 days. The temperature should be between approximately 25° C. to approximately 50° C. and more preferably 30° C. to 45° C. The optimum growth temperature is in the neighborhood of 40° C.

Any fungus belonging to the species *Talaromyces duponti* that produces transglucosidase may be employed in the present invention. In a very advantageous embodiment, the strain of *T. duponti* employed is that which is on deposit at the Fermentation Research Institute, Agency of Industrial Science and Technology, Chiba City, Japan, registered under FRI deposit number 4566. It has been unexpectedly discovered that the transglucosidase produced by this particular strain of the fungus is especiallly thermophilic as is demonstrated in the example below. Also mutant strains of FRI 4566 may be employed. Identification of *Talaromyces duponti* is further described by Cooney and Emerson in "Thermophilic Fungi", and by Awao and Mitsugi in "Trans. Mycol. Soc.", Japan, Volume 14. Additional details on this strain and its propogation are recited in U.S. Pat. No. 4,247,637.

After the *T. duponti* culture has reached the desired state of cell mass in an appropriate nutrient media, the biomass is removed by any liquid/solid separatory method, such as by filtration or by centrifugation followed with decantation. The solution containing the enzyme, i.e., filtrate or supernatant is then treated by concentration, precipitation, or a combination thereof. For instance, the solution may be concentrated by the usual methods such as ultrafiltration and/or evaporation. Then, the enzyme may be precipitated from the concentrate (or from the solution in the event there was no concentration) in the form of a cake or slurry by the addition of inorganic salts such as ammonium sulfate or sodium sulfate or the addition of organic solvents such as methanol, ethanol, or acetone. After the enzyme-containing cake is precipitated, it may be then slurried in a solution, such as water or water that has been buffered, to dissolve or extract the enzyme therefrom and provide an enzyme-containing extract. Because of pH selective elution, described further below, it is preferred to employ citrate-phosphate buffer (pH 8.0) as the extractant to dissolve the enzyme, and desirable then to dialyze the enzyme-containing buffered extract, preferably overnight.

The transglucosidase containing solution, whether obtained by a concentration method, a precipitation method or some combination thereof as described in the paragraph above, is then purified such as by treatment with clay, chromotography, or some combination thereof.

For instance, chromotography may be conducted by passing the transglucosidase containing solution through a diethylaminoethylene-cellulose (DEAE-cellulose) column, at an appropriate pH. The transglucosidase-containing solution should be buffered to a pH of approximately 7 to 9, more preferably 8, and/or the column should be equilibrated to a pH of approximately 7 to 9, more preferably 8. This is preferably accomplished with sodium citrate-phosphate buffer (pH approximately 8.0). At a pH of approximately 7 to 9, more preferably 8, the transglucosidase will be in the effluent fractions, whereas other impurities such as glucoamylase remain in the column. Additional transglucosidase is recovered by washing the colum with more buffer solution in a volume amount of at least the volume of the DEAE-cellulose. The resultant is a transglucosidase solution that is substantially free of glucoamylase and other impurities.

Alternatively, after the biomass has been removed from the nutrient growth medium, by any solid/liquid separatory technique such as those mentioned above to provide a transglucosidase-containing solution, the transglucosidase then may be isolated from this solution by adding clay, preferably particulate bentonite, at an appropriate pH, desirably between 3 and 5. Clay treatment to remove transglucosidase from a solution containing both transglucosidase and glucoamylase from Aspergillus or Rhizopus is disclosed in U.S. Pat. No. 3,042,584.

The transglucosidase forms a reaction product with the clay that coagulates and precipitates to the bottom of the solution, leaving the glucoamylase in solution. This reaction product may then be separated from the solution by any standard solid/liquid separatory technique, followed by eluting the transglucosidase from the clay with an eluting solution having a pH outside the range in which the clay and transglucosidase form a precipitate, preferably a neutral or alkaline pH.

The transglucosidase obtained from *Talaromyces duponti* is very heat stable. For instance, at 60° C., the optimum pH for activity is approximately 4.5 to 5.0. The optimum temperature of the purified transglucosidase is 70° C.

Thermodeactivation of the transglucosidase from *T. duponti* in accordance with this invention has been compared to thermodeactivation of transglucosidase from *Aspergillus niger* at 70° C. More particularly, after only 60 minutes at 70° C., transglucosidase from *A. niger* is completely deactivated, whereas over 40% of the activity still remains for transglucosidase from *T. duponti*. These thermophilic properties are further described in detail in the Tables A, B and C in the Example below.

The transglucosidase of the present invention may be employed to convert maltose into the trisaccharide panose and the disaccharide isomaltose, which are non-fermentatable sugars. The formation of these non-fermentatable oligosaccharides may be conducted by incubating a maltose-containing solution with the transglucosidase. The fermentable sugar, glucose which is also formed in the system, as well as some residual maltose will typically be present in the resultant. Incubation is conducted for 1 to 6 days, at 50°-70° C., with the pH maintained in the acid range. In a very advantageous embodiment, the incubation is carried out for 72 hours at 60° C. and pH 4.5 (0.1M sodium acetate buffer).

The following Example illustrates the preferred embodiment of the present invention and is not intended to limit the claims to the embodiment disclosed in this Example.

EXAMPLE

To a jar fermentor was added 10 liters of a liquid fermentation medium comprising 5% soluble Lintner starch, 2% corn steep liquor, 0.5% Pharmamedia ® (a cottonseed meal supplied by Trader Protein Co.), 0.5% yeast extract (supplied by Difco Laboratories, Detroit, Mich.), 0.1% dipotassium phosphate, 0.05% magnesium sulfate and 0.01% calcium chloride adjusted to pH 7.0 with 1N NaOH.

Five seed cultures were prepared by removing five 100 ml aliquots of medium from the jar fermentor and dispensing each aliquot into a 500 ml erlenmeyer flask, followed by autoclaving all five for 20 minutes at 121° C. to sterilize the medium. Each sterilized sample was then inoculated with *Talaromyces duponti* strain FRI 4566 and shaken on a rotary shaker for 6 hours at 40° C. The 5 samples were then combined to provide approximately 500 ml. The remainder of the medium was heated in the jar fermentor at 121° C. for 20 minutes and then inoculated with the 500 ml of *T. duponti* strain FRI 4566 and agitated at 40° C. for 7 days. At the end of the fermentation, the mycelia were removed from the whole fermentation broth by filtration, to provide a cell-free filtrate.

A slurry was precipitated by adding solid ammonium sulfate to the filtrate at 70% degree of saturation. The precipitate was recovered by centrifugation followed by decantation of the supernatant liquid. The enzymes were then dissolved from the precipitate in 200 ml of 0.05M citrate-phosphate buffer (pH 8.0) and dialyzed overnight against the same buffer. The dialyzed sample was passed through a DEAE-cellulose column which had been equilibrated wih 0.1M sodium citrate-phosphate buffer (pH 8.0). The column was washed with additional buffer (pH 8.0) in a volume amount equal to two times the DEAE-cellulose volume. Transglucosidase was found in the effluent fractions, while glucoamylase and other impurities remained with the DEAE-cellulose in the column. The transglucosidase containing fractions were pooled together and dialyzed overnight against deionized water. Polyacrylamide gel electrophoresis was performed in a glass tube (0.5×7 cm) containing 7.5% gel and a current of 2 ma (milliamperes) per tube for 1.5 hours at room temperature in Tris-glycine buffer (pH 8.3) according to the method described by B. J. Davis in "Annals New York Acad. Sci.", Vol. 121, p 404, (1964). The isolated transglucosidase sample was essentially pure.

The purified transglucosidase sample was used for partial characterization and panose formation. The transglucosidase activity was assayed based on the liquid chromatography quantitative measurement of a transglucosylic product, i.e., panose in an incubation mixture of enzyme and maltose at pH 4.5 and 60° C., which is a modification of the method described by Pazur et al in "Archieves of Biochemistry and Biophysics", Vol. 93, pages 43–49 (1961). A unit of transglucosidase activity is defined as the amount of enzyme which produces one micromole of panose per hour from 20% weight/volume (w/v) maltose solution at pH 4.5 and 60° C. The transglucosidase activity in the filtrate was found to be 20 units per milliliter. The formation of non-fermentable oligosaccharides from the maltose was performed as follows: 4.0 ml of 25% maltose solution pH (4.5) was incubated with 1.0 ml of enzyme solution (2.6 u/ml) for 72 hours at 60° C. and pH 4.5 (buffered with 0.1M sodium acetate). The carbohydrate profile determined by gas chromatography was as follows: 22.6% glucose, 46.4% maltose, 6.5% isomaltose and 24.6% panose.

This transglucosidase was then compared to transglucosidase from *Aspergillus niger*. Data for *A. niger* were taken from Pazur et al mentioned in the paragraph above. As shown in Table A, the optimum pH for activity of this enzyme is about 4.5–5.0 at 60° C., whereas for transglucosidase from *A. niger* it is 3.5 at 30° C. Table B shows the effect of temperature on transglucosidase activity. The optimum temperature of this purified enzyme is 70° C. Table C compares the thermal inactivation curves of the transglucosidases from *T. duponti* and *A. niger* at 70° C. As shown in this Table, the present enzyme is much more heat stable than transglucosidase from *A. niger*.

TABLE A

Effect of pH on Transglucosidase Activity

| | RELATIVE ACTIVITY (%) pH: | | | | | | | | |
|---|---|---|---|---|---|---|---|---|---|
| | 2.0 | 2.5 | 3.0 | 3.5 | 4.0 | 4.5 | 5.0 | 5.5 | 6.0 | 7.0 |
| *T. duponti* transglucosidase* | — | — | — | 58 | 71 | 100 | 98 | 84 | 61 | 44 |
| *A. niger* transglucosidase** | 51 | 78 | 84 | 100 | 73 | 56 | 51 | — | 21 | — |

*Activity was determined at 60° C. using 20% (w/v) maltose as substrate
Buffer solution
pH 3.5–5.0:0.1 M Sodium Acetate
pH 6.0–7.0:0.1 M Tris-Acetate
**Data was taken from J. P. Pazur and Tadakiko Ando, "Archives of Biochemistry and Biophysics", 93, 43–49, 1961, where activity was determined at 30° C. using 20% (w/v) maltose as substrate.

TABLE B

Effect of Temperature on *T. duponti* Transglucosidase Activity using 20% (w/v) Maltose Buffered at pH 4.5 with 0.1 M Sodium Acetate as Substrate

| Temperature (°C.) | Relative Activity (%) |
|---|---|
| 40 | 12.6 |
| 50 | 24.4 |
| 60 | 48.9 |
| 70 | 100.0 |
| 80 | 64.9 |
| 90 | 0.0 |

TABLE C

Thermostability of Transglucosidase*
Residual Activity of Transglucosidase after Incubation for the Specified Time at 70° C.

| | Min. | | | | |
|---|---|---|---|---|---|
| | 15 | 30 | 45 | 60 | 120 |
| *T. duponti* transglucosidase (at pH 4.5) | 78.5% | 68.8% | 62.4% | 41.9% | 32.3% |
| *A. niger* transglucosidase (at pH 4.0) | 17.2% | 6.3% | 4.7% | 3.1% | 0% |

*Thermostability tests of transglucosidases were carried out at 70° C. in 0.1 M acetate buffer (pH 4.5 and pH 4.0 respectively) in the absence of substrate.

We claim:

1. A method for preparing transglucosidase comprising culturing *Talaromyces duponti* FRI 4566 in a suitable nutrient medium and isolating the transglucosidase therefrom.

2. The method of claim 1 wherein the transglucosidase is isolated from the nutrient growth medium by:
   (a) removing the biomass from the nutrient growth medium to provide a transglucosidase containing solution,
   (b) treating the solution by precipitation of a transglucosidase containing cake followed with extraction of the transglucosidase therefrom to provide a transglucosidase containing extract,
   (c) purifying the transglucosidase containing extract; and
   (d) recovering purified transglucosidase substantially free of glucoamylase and other impurities.

3. The method of claim 2 wherein step (b) is preceded or followed by concentration.

4. The method of claim 2, wherein the purifying in step (c) is accomplished by passing the treated transglucosidase-containing extract resulting from step (b) through a DEAE-column at an appropriate pH, and step (d) is accomplished by recovering the transglucosidase-containing-effluent from the column.

5. The method of claim 1 wherein (a) the biomass is removed from the nutrient growth medium to provide transglucosidase containing solution, (b) transglucosidase is isolated from the transglucosidase-containing solution by adding particulate clay thereto at an appropriate pH range to cause the transglucosidase to form a reaction product with the clay, and (c) the clay/transglucosidase reaction product is recovered from the solution by a solid/liquid separatory technique.

6. The method of claim 5 further including (d) eluting the transglucosidase from the reaction product with an eluting solution having a pH range outside that which causes the clay/transglucosidase reaction product in step (b).

7. Transglucosidase produced by *T. duponti* FRI 4566 whose thermal stability is such that it retains at least 40% of its original activity after being held at 70° C. for a period of 60 minutes at pH 4.5.

8. A method for converting maltose to non-fermentable and fermentable sugars which comprises contacting the maltose with the transglucosidase of claim 7.

9. The method of claim 8, wherein contacting the maltose consists essentially of incubating maltose with the transglucosidase for 1 to 6 days, at 50° C. to 70° C. at an acidic pH, and recovering glucose, maltose, isomaltose, and panose.

* * * * *